(12) United States Patent
Sun et al.

(10) Patent No.: US 9,895,217 B2
(45) Date of Patent: Feb. 20, 2018

(54) STENT ATTACHMENT FOR ENDOVASCULAR ANEURYSM REPAIR

(75) Inventors: Jichao Sun, West Lafayette, IN (US); Natalie M. Abell, Chicago, IL (US); Neal E. Fearnot, West Lafayette, IN (US); Alan R. Leewood, Lafayette, IN (US); James D. Purdy, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1595 days.

(21) Appl. No.: 12/667,378

(22) PCT Filed: Jun. 13, 2008

(86) PCT No.: PCT/US2008/007420
§ 371 (c)(1),
(2), (4) Date: Jul. 20, 2010

(87) PCT Pub. No.: WO2008/156683
PCT Pub. Date: Dec. 24, 2008

(65) Prior Publication Data
US 2010/0280590 A1    Nov. 4, 2010

Related U.S. Application Data

(60) Provisional application No. 60/934,331, filed on Jun. 13, 2007.

(51) Int. Cl.
*A61F 2/82*    (2013.01)
*A61F 2/07*    (2013.01)
*A61F 2/89*    (2013.01)

(52) U.S. Cl.
CPC ................ *A61F 2/07* (2013.01); *A61F 2/89* (2013.01); *A61F 2002/075* (2013.01); *Y10T 29/49826* (2015.01)

(58) Field of Classification Search
CPC .............................................. A61F 2/82
(Continued)

(56) References Cited

U.S. PATENT DOCUMENTS 3,953,566 A    4/1976    Gore
4,675,361 A    6/1987    Ward, Jr.
(Continued)

FOREIGN PATENT DOCUMENTS

EP    0 893 108 A2    1/1999
EP    1 726 271 A2    11/2006
(Continued)

OTHER PUBLICATIONS

International Search Report and Written Opinion of the International Searching Authority for International Application No. PCT/US2008/007420, dated Aug. 27, 2008, 7 pages.
(Continued)

*Primary Examiner* — Matthew Schall
(74) *Attorney, Agent, or Firm* — Brinks Gilson & Lione

(57) ABSTRACT

The technology described herein relates to a stent graft and a method of making the stent wherein the stent comprises interconnected struts and is connected to the graft material by applying at least one band of polymer so as to cover at least a portion of at least some of the struts. A stent supported area is created by the stent's attachment to the graft material and the at least one band of polymer is applied so as to leave the majority of the stent supported area uncovered by the at least one band of polymer.

10 Claims, 3 Drawing Sheets

(58) Field of Classification Search
USPC .................................................. 623/1.13
See application file for complete search history.

(56) References Cited

U.S. PATENT DOCUMENTS

| | | | |
|---|---|---|---|
| 4,861,830 | A | 8/1989 | Ward, Jr. |
| 5,017,664 | A | 5/1991 | Grasel et al. |
| 5,282,823 | A * | 2/1994 | Schwartz et al. ............ 623/1.22 |
| 5,589,563 | A | 12/1996 | Ward et al. |
| 5,980,799 | A | 11/1999 | Martakos et al. |
| 6,547,815 | B2 | 4/2003 | Myers |
| 6,939,377 | B2 | 9/2005 | Jayaraman et al. |
| 8,262,720 | B2 | 9/2012 | Bonsignore et al. |
| 2002/0187288 | A1 | 12/2002 | Lim et al. |

FOREIGN PATENT DOCUMENTS

| | | |
|---|---|---|
| JP | 04-253856 | 9/1992 |
| JP | 2006-158968 A | 6/2006 |
| WO | WO 00/42949 A2 | 7/2000 |

OTHER PUBLICATIONS

Examination Report No. 1 for AU Application No. 2008266922, dated Aug. 13, 2012, 3 pages.
Office Action and English translation for JP Application No. 2010-512204, dated Dec. 11, 2012, 5 pages.
Office Action and English translation for JP Application No. 2010-512204, dated Aug. 20, 2013, 6 pages.
International Preliminary Report on Patentability for PCT/US2008/007420 dated Nov. 9, 2009, 5 pages.

* cited by examiner

STENT ATTACHMENT FOR ENDOVASCULAR ANEURYSM REPAIR

TECHNICAL FIELD

This disclosure relates to stent grafts and methods of making the same with some embodiments having sutureless stent grafts.

BACKGROUND OF THE INVENTION

The functional vessels of human and animal bodies, such as blood vessels and ducts, occasionally weaken or even rupture. For example, in the aortic artery the vascular wall can weaken, resulting in dangerous conditions such as aneurysms and dissections. Upon further exposure to hemodynamic forces, such an aneurysm can rupture.

One intervention for weakened, aneurismal, or ruptured vessels is the introduction of an endoluminal device or prosthesis, such as a stent graft, into a patient's vessel. These devices are designed to provide some or all of the functionality of the original, healthy vessel and/or preserve any remaining vascular integrity by reinforcing the portion of the vessel wall that contains the site of vessel weakness or failure. Stent grafts for endoluminal deployment are generally formed from a tube of a biocompatible material and one or more stents to maintain a lumen therethrough. Stent grafts can effectively exclude the aneurysm by sealing both proximally and distally to the aneurysm, such that the patient's blood flow is shunted through the stent graft. A device of this type can, for example, treat various arterial aneurysms, including those in the thoracic aorta, abdominal aorta, iliac, or hypogastric artery.

Two closely related aspects of stent graft function are sealing and fixation. A stent graft typically engages the wall of the lumen on both ends of the aneurysm or other defect, at proximal and distal regions referred to as landing or sealing zones. Typically these sealing zones are located near the termini of the stent grafts. The seal between the stent graft and the vascular wall is typically formed at these locations as a result of the circumferential apposition of the stent graft to the vascular wall, where this apposition is typically maintained by the radial force of the stents that are attached to the stent graft.

It is also desirable to fix, or anchor, the stent graft in place. For some abdominal aortic aneurysm stent grafts, proximal fixation in the neck region of the aorta is critical for long term durability of endoluminal repair. Fixation or anchoring of the stent graft can be achieved using a variety of anchoring mechanisms. One anchoring mechanism relies on the frictional forces that exist between the stent graft and aortic wall due to the radial force supplied by the stent. Fixation may also be achieved by using small hooks or barbs that extend from the stent graft and penetrate the arterial wall. Another method of anchoring the stent graft may involve tissue encapsulation, wherein exposed stent struts and other parts of the stent graft may eventually become completely encapsulated by tissue growth, thereby assisting fixation.

The stent and the graft material of endoluminal prostheses are often attached using hand-sewn sutures. Unfortunately, this method of attachment is labor-intensive, time-consuming, and expensive.

Another method of attaching the stent and the graft material of an endoluminal prosthesis is to cover the stent with an adhesive or a polymer coating that will allow the stent to be bonded to the graft material. Unfortunately, this type of attachment has several drawbacks. For example, these techniques often require multiple steps, since the stent must be treated with the adhesive or polymer coating before the process of attaching the graft can begin. Furthermore, the process of coating the stent with the adhesive or polymer coating usually requires multiple steps. Typically, the adhesive or coating is applied in a first step, using a variety of methods, and then must be cured in a subsequent step. In addition, once the adhesive or polymer coating has been applied to the stent and the graft material has been placed over or within the coated stent, actual bonding between the graft material and the adhesive, or the polymer coating, usually requires heating the coated stent and the graft material in an oven or other heating device. Unfortunately, this heating process limits the types of graft materials that can be used and may also affect the integrity of the graft material itself. In addition, this heating process may also thermoplastically fuse large portions of the graft material.

SUMMARY OF THE INVENTION

The present invention seeks to provide an improved stent graft, other implantable medical device provided with one or more stents and a covering and an improved method of forming a stent graft.

One aspect of the present invention provides a method of making a stent graft including providing a tubular graft formed of a graft material; attaching a stent adjacent a surface of the tubular graft to create a stent supported area of the tubular graft, wherein the stent comprises interconnected struts; wherein the strut is attached by applying at least one band of polymer so as to cover at least a portion of at least some of the struts with the graft material adjacent the at least a portion of at least some of the struts; wherein the at least one band of polymer is applied so as to leave the majority of the surface of the stent supported area uncovered by the polymer.

In one particular embodiment, there are provided methods of making sutureless stent grafts.

In another aspect of the invention, there is provided a method wherein at least one band of polymer is applied to at least one apex of the stent. There are other aspects wherein at least one band of polymer is applied to at least one elongate portion of the stent. A band of polymer can also be applied to cover all the struts.

Another aspect of the invention provides a method wherein the at least one band of polymer transects the interconnected struts.

In yet another aspect of the invention, there is provided a stent graft comprising a tubular graft formed of a graft material; a stent attached to the surface of the tubular graft to create a stent supported area; the stent comprising interconnected struts wherein the stent is attached to the tubular graft by at least one band of polymer that covers at least a portion of at least some of the struts such that a majority of the stent supported area is uncovered by the at least one band of polymer.

The stent graft is preferably a sutureless stent graft.

BRIEF DESCRIPTION OF THE DRAWING

Embodiments of the present invention are described below, by way of example only, with reference to the accompanying drawings, in which.

DETAILED DESCRIPTION

Figure 1A:
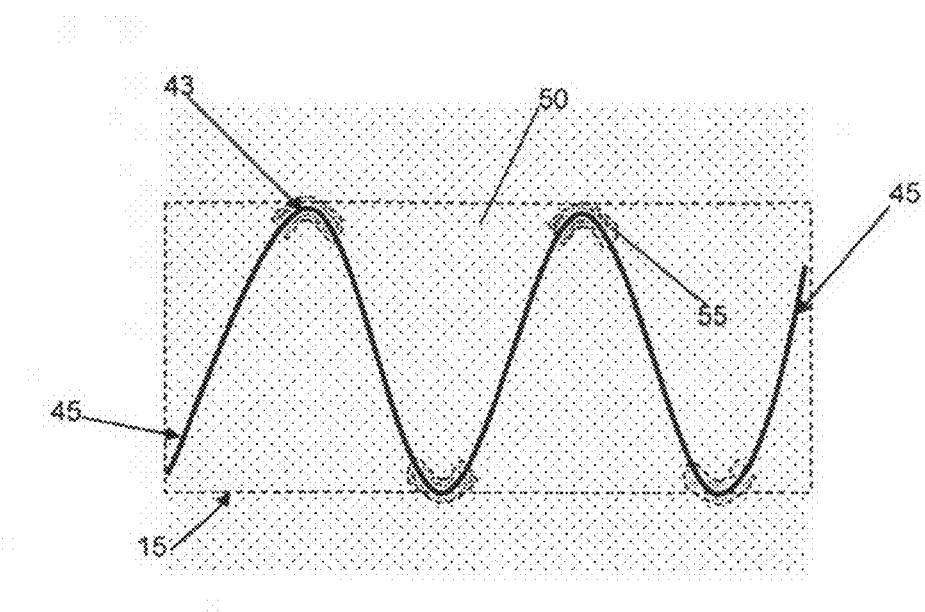
FIG. 1A is a view of a sinuously shaped stent on a graft material laid flat that has polymer applied at the apices of the stent.

Throughout this specification, when discussing the application of this invention to the aorta, the term distal, with respect to a prosthesis, is intended to refer to the end of the prosthesis furthest away in the direction of blood flow from the heart, and the term proximal is intended to mean the end of the prosthesis that, when implanted, would be nearest to the heart.

The term "prosthesis" means any replacement for a body part or for a function of that body part; or any device that enhances or adds functionality to a physiological system.

The term "endovascular" describes objects that are found or can be placed inside the vasculature of the human or animal body. This includes lumens such as blood vessels, parts of the gastrointestinal tract, ducts such as bile ducts, parts of the respiratory system, etc. "Endovascular prosthesis" thus describes a prosthesis that can be placed inside one of these lumens.

The term "graft or graft material" means a generally cannular or tubular member which acts as an artificial vessel or prosthesis. A graft by itself or with the addition of other elements, such as structural components, can be an endoluminal prosthesis. The graft comprises a single material, a blend of materials, a weave, a laminate, or a composite of two or more materials.

The term "structural component" means any device that is attached to a prosthesis, such as a stent graft. For example, structural components may comprise stents, radiopaque markers, anchoring stents, barbs, and lateral support rings for supporting a fenestration. The structural components may be attached to the exterior of the graft, the interior of the graft, the exterior of the graft, and/or may be sandwiched between two or more layers of graft material.

The structural components may be made from numerous base materials, such as: biocompatible metals or other metallic materials; polymers including bioabsorbable or biostable polymers; stainless steels (e.g., 316, 316L or 304); nickel-titanium alloys including shape memory or superelastic types (e.g., nitinol or elastinite); noble metals including platinum, gold, or palladium; refractory metals including tantalum, tungsten, molybdenum, or rhenium; stainless steels alloyed with noble and/or refractory metals; silver; rhodium; inconel; iridium; niobium; titanium; magnesium; amorphous metals; plastically deformable metals (e.g., tantalum); nickel-based alloys (e.g., including platinum, gold, and/or tantalum alloys); iron-based alloys (e.g., including platinum, gold, and/or tantalum alloys); cobalt-based alloys (e.g., including platinum, gold, and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; magnetic ferrite; nonmetallic biocompatible materials including polyamides, polyolefins (e.g., polypropylene or polyethylene), nonabsorbable polyesters (e.g., polyethylene terephthalate) or bioabsorbable aliphatic polyesters (e.g., homopolymers or copolymers of lactic acid, glycolic acid, lactide, glycolide, para-dioxanone, trimethylene carbonate, or .epsilon.-caprolactone); polymeric materials (e.g., poly-L-lactic acid, polycarbonate, polyethylene terephthalate, or engineering plastics such as thermotropic liquid crystal polymers (LCPs)); biocompatible polymeric materials (e.g., cellulose acetate, cellulose nitrate, silicone, polyethylene terephthalate, polyurethane, polyamide, polyester, polyorthoester, polyanhydride, polyether sulfone, polycarbonate, polypropylene, high molecular weight polyethylene, or polytetrafluoroethylene); degradable or biodegradable polymers, plastics, natural (e.g., animal, plant or microbial) or recombinant material (e.g., polylactic acid, polyglycolic acid, polyanhydride, polycaprolactone, polyhydroxybutyrate valerate, polydepsipeptides, nylon copolymides, conventional poly(amino acid) synthetic polymers, pseudo-poly(amino acids), or aliphatic polyesters (e.g., polyglycolic acid (PGA), polylactic acid (PLA), polyalkylene succinates, polyhydroxybutyrate (PHB), polybutylene diglycolate, poly epsilon-caprolactone (PCL), polydihydropyrans, polyphosphazenes, polyorthoesters, polycyanoacrylates, polyanhydrides, polyketals, polyacetals, polyalpha-hydroxy-esters), poly(carbonates), poly (imino-carbonates), poly(beta-hydroxy-esters) or polypeptides)); polyethylene terephthalate (e.g., Dacron® or Mylar®); expanded fluoropolymers (e.g., polytetrafluoroethylene (PTFE)); fluorinated ethylene propylene (FEP); copolymers of tetrafluoroethylene (TFE) and per fluoro (propyl vinyl ether) (PFA)); homopolymers of polychlorotrifluoroethylene (PCTFE) and copolymers with TFE; ethylene-chlorotrifluoroethylene (ECTFE); copolymers of ethylene-tetrafluoroethylene (ETFE); polyvinylidene fluoride (PVDF); polyvinyfluoride (PVF); polyaramids (e.g., Kevlar®); polyfluorocarbons including polytetrafluoroethylene with and without copolymerized hexafluoropropylene (e.g., Teflon® or Goretex®); expanded fluorocarbon polymers; polyglycolides; polylactides; polyglycerol sebacate; polyethylene oxide; polybutylene terephthalate; polydioxanones; proteoglycans; glycosaminoglycans; poly(alkylene oxalates); polyalkanotes; polyamides; polyaspartimic acid; polyglutarunic acid polymer; poly-p-diaxanone (e.g., PDS); polyphosphazene; polyurethane including porous or nonporous polyurethanes; poly(glycolide-trimethylene carbonate); terpolymer (copolymers of glycolide, lactide or dimethyltrimethylene carbonate); polyhydroxyalkanoates (PHA); polyhydroxybutyrate (PHB) or poly(hydroxybutyrate-co-valerate) (PHB-co-HV); poly(epsilon-caprolactone) (e.g., lactide or glycolide); poly(epsilon-caprolactone-dimethyltrimethylene carbonate); polyglycolic acid (PGA); poly-L and poly-D (lactic acid) (e.g., calcium phosphate glass); lactic acid/ethylene glycol copolymers; polyarylates (L-tyrosine-derived) or free acid polyarylates; polycarbonates (tyrosine or L-tyrosine-derived); poly(ester-amides); poly (propylene fumarate-co-ethylene glycol) copolymer (e.g., fumarate anhydrides); polyanhydride esters; polyanhydrides; polyorthoesters; prolastin or silk-elastin polymers (SELP); calcium phosphate (bioglass); compositions of PLA, PCL, PGA ester; polyphosphazenes; polyamino acids; polysaccharides; polyhydroxyalkanoate polymers; various plastic materials; Teflon®; nylon; block polymers or copolymers; Leica RM2165; Leica RM2155; organic fabrics; biologic agents (e.g., protein, extracellular matrix component, collagen, fibrin); small intestinal submucosa (SIS) (e.g., vacuum formed SIS); collagen or collagen matrices with growth modulators; aliginate; cellulose and ester; dextran; elastin; fibrin; gelatin; hyaluronic acid; hydroxyapatite;

polypeptides; proteins; ceramics (e.g., silicon nitride, silicon carbide, zirconia, or alumina); bioactive silica-based materials; carbon or carbon fiber; cotton; silk; spider silk; chitin; chitosan (NOCC or NOOC-G); urethanes; glass; silica; sapphire; composites; any mixture, blend, alloy, copolymer or combination of any of these; or various other materials not limited by these examples.

The term "stent" means any device that provides rigidity, expansion force, or support to a prosthesis, such as a stent graft. In one configuration, the stent may represent a plurality of discontinuous devices. In another configuration, the stent may represent one device or a plurality of interconnected struts. Stents may have a wide variety of configurations and may be balloon-expandable or self-expanding. Typically, stents have a circular cross-section when fully expanded, so as to conform to the generally circular cross-section of a body lumen. In one example, a stent may comprise elongate portions and acute bends or apices that are between the elongate portions. The stents may be arranged in a zigzag or sinuous configuration in which the struts are set at angles to each other and are connected the curvilinear portions.

A variety of biocompatible materials may be employed to construct the stent, or portions of the stent, including metals and/or alloys, medically-acceptable polymers and/or bioabsorbable polymers or materials. The metals and/or alloys may, among other things, include stainless steel, tantalum, nitinol, gold, silver, tungsten, platinum, inconel, cobalt-chromium alloys and iridium, all of which are commercially available metals or alloys used in the fabrication of medical devices. In a preferred configuration, the stent is constructed from nitinol, stainless steel and/or cobalt-chromium alloys.

The term "partial stent" means a stent that does not form a complete tubular shape, and is typically configured as a stent that has been divided along its axis or parallel to its axis.

The term "stent graft" means a stent that has been connected to a graft. A stent can be connected the interior of the graft, the exterior of the graft, and/or sandwiched between two layers of graft material. A stent can also be secured to one of the openings of the graft such that the stent extends from the graft.

"Biocompatible" describes something that can be substantially non-toxic in the in vivo environment of its intended use, and is not substantially rejected by the patient's physiological system (i.e., is non-antigenic). This can be gauged by the ability of a material to pass the biocompatibility tests set forth in International Standards Organization (ISO) Standard No. 10993, and/or the U.S. Pharmacopeia (USP) 23, and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity, and/or immunogenicity. A biocompatible structure or material, when introduced into a majority of patients, will not cause a significantly adverse reaction or response. Furthermore, biocompatibility can be affected by other contaminants such as prions, surfactants, oligonucleotides, and other agents or contaminants.

Attaching the stents to the woven graft material provides the stent graft, which extends between a stent graft proximal end and a stent graft distal end. The stents are made from a base material. Preferably, the base material that forms the stents is a metal, such as stainless steel; a shape memory alloy, such as nitinol; or other biocompatible alloys. More preferably, the base material that forms the stents is a stainless steel.

The graft material is a biocompatible material that is both flexible and abrasion resistant. Furthermore, the graft material should be selected from those materials that are particularly well suited for thermoplastic deformation, such that the material can be thermoplastically fused to a stent. Preferably, the woven graft material is woven polyester. More preferably, the woven graft material is a polyethylene terephthalate (PET), such as DACRON® (DUPONT, Wilmington, Del.) or TWILLWEAVE MICREL® (VASCUTEK, Renfrewshire, Scotland). Woven polyesters, such as Dacron, possess varying degrees of porosity, where the degree of porosity can be selectively controlled based on the weaving or knitting process that is used to produce the woven polyester. Consequently, depending on the application, the porosity can be adjusted to encourage incorporation of a patient's tissue into the woven graft material, which in turn may more securely anchor the prosthesis within the patient's vessel or lumen. Furthermore, the degree of porosity can also be adjusted to provide a woven graft material that is impermeable to liquids, including blood or other physiological fluids.

The polymer used in the present invention that may be preferred comprises polyurethane or other polymer suitable for use in making a stent graft. Examples of polyurethanes include Thoralon® (THORATEC, Pleasanton, Calif.), BIOSPAN®, BIONATE®, ELASTHANE®, PURSIL®, and CARBOSIL® (POLYMER TECHNOLOGY GROUP, Berkeley, Calif.). As described in U.S. Pat. No. 6,939,377, incorporated herein by reference, Thoralon® is a polyetherurethane urea blended with a siloxane-containing surface modifying additive. Specifically, the polymer is a mixture of base polymer BPS-215 and an additive SMA-300. The concentration of additive may be in the range of 0.5% to 5% by weight of the base polymer. The BPS-215 component (THORATEC) is a segmented polyether urethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). The SMA-300 component (THORATEC) is a polyurethane comprising polydimethylsiloxane as a soft segment and the reaction product of MDI and 1,4-butanediol as a hard segment. A process for synthesizing SMA-300 is described, for example, in U.S. Pat. Nos. 4,861,830 and 4,675,361, which are incorporated herein by reference. A polymer graft material can be formed from these two components by dissolving the base polymer and additive in a solvent such as dimethylacetamide (DMAC) and solidifying the mixture by solvent casting or by coagulation in a liquid that is a non-solvent for the base polymer and additive.

Thoralon® has been used in certain vascular applications and is characterized by thromboresistance, high tensile strength, low water absorption, low critical surface tension, and good flex life. Thoralon® is believed to be biostable and to be useful in vivo in long term blood contacting applications requiring biostability and leak resistance. Because of its flexibility, Thoralon® is useful in larger vessels, such as the abdominal aorta, where elasticity and compliance is beneficial.

Other polyurethane ureas may be used in addition to Thoralon®. For example, the BPS-215 component with a MDI/PTMO mole ratio ranging from about 1.0 to about 2.5 may be used.

In addition to polyurethane ureas, other polyurethanes, preferably those having a chain extended with diols, may be used as the graft material. Polyurethanes modified with cationic, anionic, and aliphatic side chains may also be used. See, for example, U.S. Pat. No. 5,017,664, which is incorporated herein by reference. Polyurethanes may need to be dissolved in solvents such as dimethyl formamide, tetrahydrofuran, dimethyacetamide, dimethyl sulfoxide, or mixtures thereof.

The polyurethanes may also be end-capped with surface active end groups, such as, for example, polydimethylsiloxane, fluoropolymers, polyolefin, polyethylene oxide, or other suitable groups. See, for example, the surface active end groups disclosed in U.S. Pat. No. 5,589,563, which is incorporated herein by reference.

In one embodiment, the graft material may contain polyurethane having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. Examples of siloxane-polyurethanes are disclosed in U.S. Pat. Pub. No. 2002/0187288 A1, which is incorporated herein by reference.

The graft may contain polytetrafluoroethylene or expanded polytetratfluoroethylene (ePTFE). The structure of ePTFE can be characterized as containing nodes connected by fibrils. The structure of ePTFE is disclosed, for example, in U.S. Pat. Nos. 6,547,815 B2; 5,980,799; and 3,953,566; all of which are incorporated herein by reference.

The preferred embodiment described herein provides a method of making a stent graft, in some embodiments that may be preferred a sutureless stent graft. The method comprises providing a tubular graft formed of a graft material and placing a stent adjacent to at least one surface of the tubular graft. The graft material can comprise biocompatible graft material. As described above, the biocompatible graft material is preferably both flexible and abrasion resistant. In some embodiments that graft material is a woven graft material and in some embodiments that may be preferred the graft material is woven polyester. In another embodiment, the graft material may be made of a single material, or it may be a blend, weave, laminate, or composite of two or more materials. The graft material may also include other additives, such as plasticizers, compatibilizers, surface modifiers, biological materials such as peptides and enzymes, and therapeutic agents such as drugs or other medicaments.

The biocompatible graft material is shaped into a tubular form using methods known in the art to form a tubular graft. The tubular graft has an interior and an exterior surface. In the method of the present invention, a stent is placed adjacent to at least one surface of the graft. In one embodiment, a stent may be attached to the exterior of the graft material. In another embodiment, a stent may be attached to the interior of the graft material. The tubular graft can comprise more than one layer of graft material. In such embodiments, a stent may be placed between two layers of graft material such that the stent is adjacent to the exterior of one tubular graft and adjacent to the interior of another tubular graft.

The present invention provides, in some embodiments, a stent graft comprising a tubular graft formed of a graft material. The stent is adjacent to at least one surface of the tubular graft. The stent is also formed of interconnected struts and is attached to the tubular graft by at least one band of polymer that covers at least a portion of at least some of the struts such that a majority of the stent supported area is uncovered by the at least one band of polymer.

The at least one band of polymer is applied to bond with the graft material adjacent to the at least a portion of at least some of the struts to thereby attach the stent to the graft. In some embodiments, the polymer is applied along the path of the stent. There are also embodiments wherein the polymer is applied in a manner that transects the interconnected struts of the stent. In other embodiments that may be preferred, the liquid polymer is applied over a stencil of the outline of the stent. The polymer can be applied by using methods known in the art, for instance, spraying, ultrasonic welding, adhesive bonding, dipping, electrospinning, or casting. The polymer can also be rolled or brushed onto the stent graft.

Figure 1B:
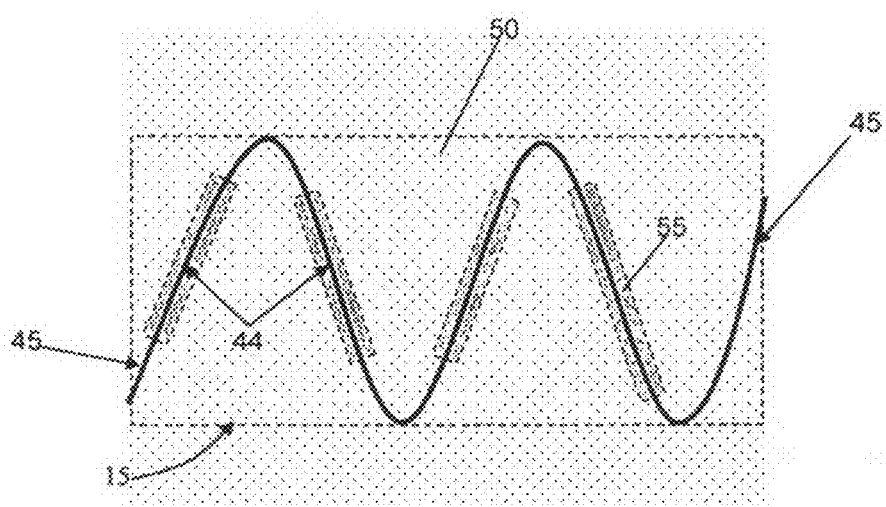
FIG. 1B is a view showing a sinuously shaped stent with polymer applied on the elongate portions of the stent.
Figure 3:
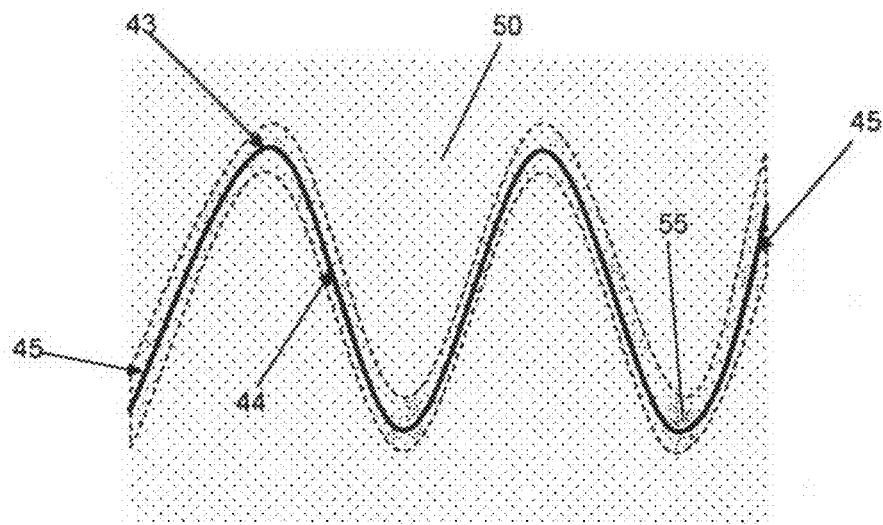
FIG. 3 is a drawing of a sinuously shaped stent attached without sutures to a graft material by application of a polymer band that covers all the struts.

One of the goals of the preferred embodiment is to provide a method of making a stent graft using less polymer than what may be used in methods known in the art while providing strong stent-to-graft bonds. Another goal is to provide sutureless stent grafts in some embodiments. In the preferred embodiment the polymer is applied such that the majority of the stent supported area 15 of the tubular graft is left uncovered by polymer. In some embodiments, at least one band of polymer is applied to at least one apex of the stent. In FIG. 1A, bands of polymer 55 have been applied at the apices 43 of the struts 45 of a zigzag stent. In FIG. 1B, bands of polymer 55 are applied along the elongate portions 44 of the struts 45. A band of polymer 55 can also be applied along both the apices 43 and elongate portions 44 such that the band of polymer 55 covers the entire strut 45 as seen in FIG. 3. In all embodiments, the bands of polymer are applied so as to leave a majority of the stent supported area 15 of the graft uncovered by the polymer.

Figure 2:
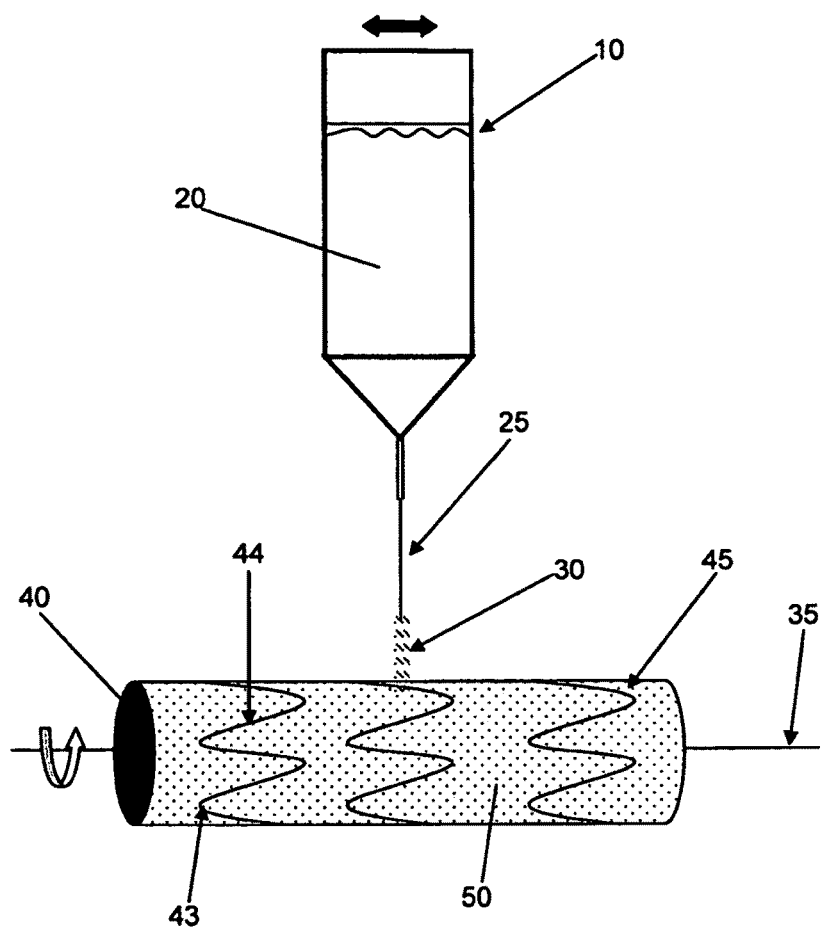
FIG. 2 illustrates the application of polymer onto a stent placed adjacent to the exterior surface of a tubular graft.

FIG. 2 is a simplified illustration of a preferred method of utilizing an electrospinning device for applying polymer 20. In this embodiment, liquid polymer 20 is generated by either heating the polymer 20 until it achieves a plastic state or mixing the polymer 20 with a solvent to form a solution. The liquid polymer 20 may be loaded into a syringe-like container 10 that is fluidly connected to a blunt needle 27 to form a spinneret. The needle 27 may have a distal opening through which the liquid polymer 20 may be ejected by a controlled force, such as by a plunger, but can be any appropriate controllable variable rate fluid displacement system and should be automated to ensure accurate flow rates.

The liquid polymer 20 is within a syringe-like container 10 and is sprayed from a nozzle 25. The stent graft 40 is provided on an axis 35 such that it can rotate about the axis 360°. In some embodiments, as the stent graft 40 rotates, the liquid polymer 20 is sprayed from the nozzle 25 in a narrow dispersion 30 sinuously on the struts 45. The width of the liquid polymer 20 applied is sufficient to encapsulate the exposed sides of the struts 45 and the graft material 50 lying immediately on either side of the struts 45. The liquid polymer 20 can be applied in a dispersion 30 having a width selected as a function of the degree of a load transfer required to distribute the movement of the stent graft 40. The width is usually calculated before the process has begun. In some embodiments the width is constant. There are also embodiments that may be preferred where the polymer 20 is applied intermittently along the struts 45 and others where the polymer is applied continuously.

The nozzle 25 can move side-to-side (as depicted by the arrows) following the path of the struts 45 depicted in FIG. 2 as the stent graft 40 rotates about the axis 35. FIG. 3 illustrates a portion of an endovascular prosthesis laid flat where the struts 45 have been attached to the graft material 50 by applying polymer 55 in a sinuous fashion. In such an embodiment, the nozzle 25 moves sinuously such that it shadows the path of a zigzag stent.

Figure 4:
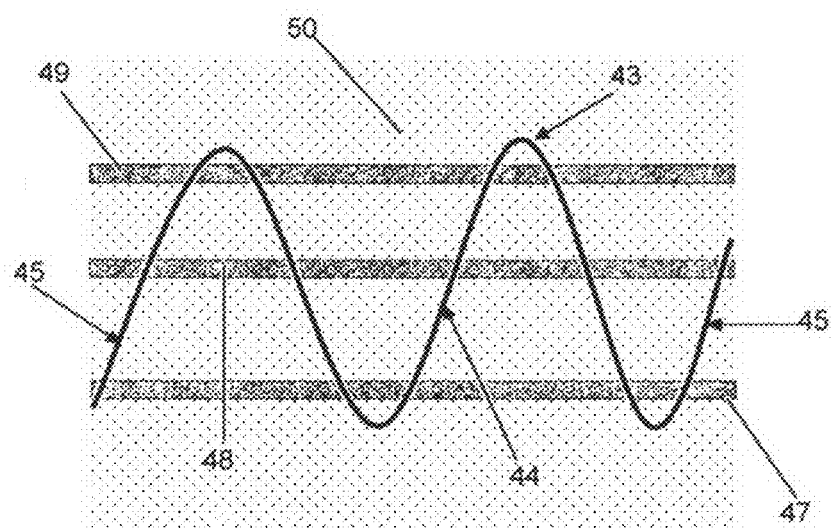
FIG. 4 depicts a stent attached without sutures to a graft material in distinct bands that transect the interconnected struts.

In some embodiments, polymer 55 is applied in a manner that transects the interconnected struts 45. As seen in FIG. 4, at least one band of polymer transects the struts 45 at their curvilinear portions 43 or the elongate portions 44. In some embodiments that may be preferred, polymer 20 is applied in three distinct bands 47, 48, and 49. Bands 47 and 49 cross the curvilinear portions 43 of the struts 45. Band 48 crosses the elongate portions 44 of the struts 45. There are embodiments that may be preferred wherein there is at least one band of polymer that transects the struts. Once the liquid polymer 20 has been applied, the endovascular prosthesis 40 is cured by means known in the art.

It is therefore intended that the foregoing detailed description be regarded as illustrative rather than limiting, and that it be understood that it is the following claims, including all equivalents, that are intended to define the scope of this invention.

The invention claimed is:

1. A stent graft comprising a tubular graft formed of a graft material; a stent attached to a surface of the tubular graft to create a stent supported area; the stent comprising interconnected struts interconnected by apices in an undulating configuration; wherein the stent is attached to the tubular graft by at least one band of polymer that leaves the majority of the tubular graft uncovered by the at least one band of polymer and wherein the band of polymer covers every strut and every apex of the stent and follows the undulating configuration, and wherein the width of the band encapsulates only an outer surface of the apices and struts and the sides of the struts and the apices and the graft material lying immediately on either side of the struts and about the apices, without covering an inner surface of the apices and struts.

2. The stent graft of claim 1, wherein the polymer comprises polyurethane.

3. The stent graft of claim 1, wherein the tubular graft comprises an interior surface and the stent is adjacent to the interior surface.

4. The stent graft of claim 1, wherein the tubular graft comprises an exterior surface and the stent is adjacent to the exterior surface.

5. The stent graft of claim 1, wherein the graft material comprises a biocompatible polyester or polyethylene terephthalate.

6. A stent graft comprising a tubular graft formed of a graft material; a stent attached to a surface of the tubular graft to create a stent supported area; the stent comprising interconnected struts and apices; and a polymer coating, wherein the polymer coating contacts at least a portion of the stent and adheres the stent to the graft material, and wherein the graft material remains substantially uncoated, wherein the band of polymer extends circumferentially about the tubular graft and covers every strut and every apex of the stent, and wherein the width of the band encapsulates only an outer surface and the sides of the struts and the apices without covering an inner surface of the struts and apices and is disposed on the graft material lying immediately on either side of the struts and about the apices, such that each strut and each apex is directly adhered to the graft by the polymer coating.

7. The stent graft of claim 6, wherein the stent has a contour and the polymer coating follows the contour of the stent.

8. The stent graft of claim 6, wherein the stent comprises a sinusoidal pattern and the coating at least partially follows the sinusoidal pattern.

9. The stent graft of claim 6, wherein the polymer coating is applied to the stent at every apex of the stent.

10. The stent graft of claim 6, wherein the stent graft comprises a plurality of stent rings with spaces of graft material between the stent rings and wherein the polymer coating does not extend into the area between the stent rings.

\* \* \* \* \*